US00PP30661P3

(12) United States Plant Patent
Cain

(10) Patent No.: US PP30,661 P3
(45) Date of Patent: Jul. 9, 2019

(54) SWEET CHERRY TREE NAMED 'IFG CHER-FIVE'

(50) Latin Name: *Prunus avium*
Varietal Denomination: IFG Cher-five

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 155 days.

(21) Appl. No.: 15/530,772

(22) Filed: Feb. 28, 2017

(65) Prior Publication Data

US 2018/0249612 P1 Aug. 30, 2018

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/08; A01H 6/7445
See application file for complete search history.

*Primary Examiner* — Keith O. Robinson

(57) ABSTRACT

This invention is a new and distinct sweet cherry tree denominated 'IFG Cher-five'. The new sweet cherry tree is characterized by producing large size dark red fruits having flat-round shape. Fruits ripen early about Apr. 25, 2014 in Delano Calif. The 'IFG Cher-five' has firm, medium acid fruit with an excellent cherry flavor. Fruits are tolerant of rain induced cracking, and high temperature induced doubling.

1 Drawing Sheet

Latin name of the genus and species claimed: *Prunus avium.*

Variety denomination: 'IFG Cher-five'.

BACKGROUND OF THE INVENTION

The new and distinct sweet cherry tree described and claimed herein originated from open pollinated seeds collected in May 2001 of the non-patented 'Flavor Giant' variety (female parent) growing in a commercial orchard in Kern County, Calif. The male pollen parent is unknown. The seeds were stratified, germinated and the resulting 231 seedlings were planted in the field near Delano, Kern County, Calif. in April 2002. The present variety of sweet cherry tree was selected as a single plant in May 2005 and was first asexually propagated in January 2006 by grafting onto *Prunus mahalab* rootstock. This propagule was found to reproduce true-to-type by asexual propagation. All propagation was done near Delano, Kern County Calif.

BRIEF SUMMARY OF THE INVENTION

Sweet cherries have traditionally been grown in climates with long cold winters and cool to moderately warm summers. Such climates provide enough cold winter temperatures to allow normal growth to resume in the spring and summer temperatures that are low enough not to induce production of unmarketable double or spurred fruit, but it limits the seasonality that cherries are available. The sweet cherry breeding program focuses on developing types of cherries that will grow in regions with low winter chilling and high summer temperatures so that the fruit will ripen before fruit in traditional growing regions.

The new sweet cherry tree 'IFG Cher-five' is characterized by producing large size dark red fruits having flat-round shape. Fruits ripen early about zero to two days ahead of the 'Brooks' variety (U.S. Plant Pat. No. 6,676). The 'IFG Cher-five' has firm, medium acid fruit with an excellent cherry flavor. Fruits are more tolerant of rain induced cracking than 'Brooks'. The tree has a medium-low chilling requirement, slightly lower than the 'Brooks' variety. It produces fewer doubled and spurred fruits as compared to the 'Brooks' variety in high summer temperature regions such as the Southern San Joaquin Valley of California. Fruits of 'IFG Cher-five' have medium long, thick stems that remain attached and stay green during storage and shipping. It has more desirable darker red skin and flesh than the 'Brooks' variety and exhibits less pitting and stores better than the 'Brooks' variety.

In comparison with the 'Glenred' (U.S. Plant Pat. No. 12,859), the 'IFG Cher-five' ripens about two to four days earlier. The fruit stems of 'IFG Cher-five' are substantially shorter than 'Glenred' and remain attached better during storage and shipping.

Compared to its female parent, the 'Flavor Giant' variety, 'IFG Cher-five' produces larger, firmer fruit.

BRIEF DESCRIPTION OF THE DRAWING

The accompanying photographic drawing in FIG. 1 illustrates in full color 'IFG Cher-five', taken from a 13-year old tree. The photograph was taken outdoors with indirect lighting. The colors are as nearly true as is reasonably possible in a color representation of this type. An actively growing shoot tip collected at harvest can be seen in the upper portion of the drawing. Typical mature fruit and fruit in cross-section and cleaned and dried fruit pits are displayed on the lower half of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Board for Plant Genetic Resources (IBPGR) 'Cherry Descriptor List' (*Prunus* spp.) (1985) which was developed with full support from the Commission of the European Communities (CEC) Programme Committee for Plant Disease Resistance Breeding and the Use of Genebanks.

The descriptive matter which follows pertains to 'IFG Cher-five' plants grown in the vicinity of Delano, Kern County, Calif. during 2013 and 2014, and is believed to apply to plants of the variety grown under similar conditions of soil and climate elsewhere:

TREE

General:

*Age*.—13 yrs. old.
*Height*.—About 3.1 M when pruned.
*Width*.—About 2.6 M when pruned.
*Vigor*.—Medium.
*Density of foliage*.—Dense.
*Form*.—Upright.
*Branching*.—Medium.
*Rootstock*.—*Prunus mahaleb*.
*Resistance to*.—Insects: Average typical of *Prunus avium* species. Diseases: Average typical of *Prunus avium* species.
*Chilling requirements*.—Medium low, slightly lower than the 'Brooks' variety.
*Graft compatibility*.—Good; produces compatible graft unions with *Prunus avium*, 'Mazzard' seedlings (non-patented) and *Prunus mahaleb* seedlings (non-patented).

Trunk:

*Trunk diameter of* 13-*year old tree,* 30 *cm above the soil line*.—About 20.1 cm.
*Lenticel size*.—Large.
*Lenticel dimensions*.—Length: About 1.2 cm. Width: About 0.4 cm.
*Lenticel shape*.—Elliptical shape oriented horizontally.
*Lenticel color*.—Grey: 201C.
*Trunk surface texture*.—Medium to slightly rough.
*Outer bark color*.—The following colors were observed: Grey: 201C and Greyed-orange: 176B.

BRANCHES 1-year old wood:

*Vertical top growth length*.—About 31.2 cm.
*Horizontal growth length*.—About 37.6 cm.
*Diameter*.—Vertical growth: About 1.3 cm. Horizontal Growth: About 0.8 cm.
*Internode length*.—About 3.9 cm.
*Number of lenticels*.—Medium: Approximately 6 lenticels per linear cm.
*Lenticel size*.—Small.
*Lenticel dimensions*.—Length: About 0.1cm. Width: About 0.1 cm.
*Lenticel shape*.—Round.
*Bark color*.—The following colors were observed: Greyed-orange; 166A and 166B.

2-year old wood:

*Length*.—About 54 cm.
*Diameter*.—About 1.4 cm.
*Internode length*.—About 5.1 cm.
*Number of lenticels*.—Medium: Approximately 7 lenticels per linear cm.
*Lenticel dimensions*.—Length: About 0.1 cm. Width: About 0.2 cm.
*Lenticel shape*.—Elliptical shape oriented horizontally.
*Number of fruiting spurs on* 2-*year wood*.—4 to 12, Average: 7.
*Bark color*.—The following colors were observed: Greyed-orange: 174A and 177B.

BUDS

Vegetative buds:

*Shape*.—Elongated.
*Vegetative bud dimensions*.—Length: About 1.0 cm. Width: About 0.4 cm.
*Vegetative bud burst*.—About Feb. 27, 2014.

Flower buds:

*Flower bud dimensions*.—Length: About 1.0 cm. Width: About 0.5 cm.
*Shape*.—Oval.
*Placement*.—At bud positions 1 to 8 on 1-year wood.
*Average number of flower buds on first year wood*.—About 8.
*Number of flower buds per spur on second year wood*.—2 to 3, Average: About 3.
*Color*.—The following colors were observed: Greyed-orange: 166A and 177A.
*Flower bud burst*.—About Mar. 1, 2014.

LEAVES

Mature leaves:

*Leaf dimensions*.—Length: About 12.1 cm. Width: About 5.0 cm.
*Leaf shape*.—Lanceolate: symmetric on both sides of central axis.
*Shape of tip*.—Acuminate: broadly.
*Shape of base*.—Attenuate.
*Margin*.—Serrated: regular, rounded.
*Leaf profile*.—Involute.

Upper surface:

*Upper surface pubescence*.—None.
*Upper leaf surface color*.—Green: 139A.
*Surface texture*.—Smooth.

Lower surface:

*Lower surface pubescence*.—Very sparse.
*Lower leaf surface color*.—Yellow-green: 147B.

Petiole:.

*Petiole dimensions*.—Length: About 4.8 cm. Width: About 1.6 mm
*Upper surface of petiole color*.—Yellow-green: 144A.
*Lower surface of petiole color*.—Yellow-green: 144B.
*Petiole groove*.—Medium: Approximately 0.9 mm.
*Petiole pubescence*.—Very sparse: only on upper surface.
*Venation*.—Arcuate.
*Vein color*.—Yellow-Green: 145A.

Glands:

*Number of glands*.—1 to 2.
*Gland dimensions*.—Length: About 0.2 cm. Width: About 1.2 cm.
*Gland shape*.—Globose.

*Gland location*.—On petiole.
*Gland color*.—Red-purple: 60A.
*Leaf stipule*.—Not present.

Flowers:
*Blooming period*.—Early.
*Blooming dates*.—First bloom Mar. 4, 2014. Full bloom Mar. 17, 2014.
*Number of flowers per cluster*.—2-3. Average: about 2.
*Corolla*.—Composed of unfused petals, somewhat overlapping.
*Corolla diameter*.—About 3.2 cm.
*Petal number*.—5.
*Petal length*.—About 1.4 cm.
*Petal width*.—About 1.4 cm.
*Margin waviness*.—Strong.
*Division of upper margin*.—Entire.
*Color of petal upper surface*.—White: 155D.
*Color of petal lower surface*.—White: 155C.
*Peduncle*.—Length: About 1.9 cm. Width: About 0.1 cm.
*Peduncle color*.—Yellow-green: 144B.
*Number of sepals*.—5.
*Sepal length*.—About 0.7 cm.
*Sepal width*.—About 0.5 cm.
*Sepal shape*.—Triangular.
*Sepal color*.—Upper surface: Yellow-green: 144A. Lower surface: Red-purple: 59C.
*Filament*.—Length: About 0.5-1.5 cm. Width: About 0.3 mm.
*Filament color*.—White: N155C.
*Anther color*.—Yellow-orange: 22D.
*Pollen color*.—Greyed-orange: 163A.
*Pollen production*.—Medium.
*Self-compatibility of flowers*.—Self-incompatible.
*Flower compatibility group*.—S1S new unidentified allele.

FRUIT

General:
*Ripening period*.—Early: Approximately: Apr. 25-30, 2014.
*Use*.—Fresh market.
*Keeping quality*.—Good: slightly better than the 'Brooks' variety.
*% Titratable acidity*.—About 0.82%.
*Refractometer test*.—Soluble solids: About 20.2 brix.
*Firmtech II* (*g/mm*).—About 280 to 339.
*Flavor*.—Excellent, good sugar/acid balance with pronounced cherry flavor.
*Juice color*.—Greyed-purple: 187B.
*Juice amount*.—Juicy.
*Eating quality*.—Excellent.

Stem:
*Stem*.—Length: About 2.6 cm. Width: About 0.2 cm.
*Stem color*.—The following colors were observed: Yellow-green: 143C and 144B.
*Stem cavity*.—Medium.
*Stem retention during storage*.—Very good.
*Stem storage quality*.—Good.

Berry:
*Uniformity of size*.—Uniform.
*Shape*.—Flat-round.
*Fruit weight*.—About 10.6 gm.
*Apical diameter*.—About 2.5 cm.
*Diameter transversely across suture*.—About 2.8 cm.
*Diameter at right angle to suture plane*.—About 2.3 cm.
*Suture*.—None.
*Percent of excessively deep or split sutures*.—0%.
*Doubles*.—0%.

Skin:
*Texture*.—Mostly smooth, with very little indentation noted at lenticels.
*Skin color*.—Greyed-purple: 187B.
*Tendency to tip crack*.—Not susceptible.
*Tendency to stem cavity crack*.—Not susceptible.

Flesh:
*Texture*.—Firm.
*Color*.—The following colors were observed: Greyed-purple: 187A, and Red: 45C and 45D and 50A.

Stone:
*Shape*.—Ovate.
*Length*.—About 1.3 cm.
*Width transversely across suture*.—About 1.0 cm.
*Width at right angle to suture plane*.—About 1.1 cm.
*Type*.—Semi-cling.
*Surface texture*.—Slightly rough.
*Stone color when dry*.—Yellow-white: 158A.
*Tendency to split*.—None.
*Base*.—Broadly pointed.
*Apex*.—Acutely pointed.
*Ventral edge*.—Prominent narrow suture extending from the base to the midpoint of the stone subtended by 2 minor ridges converging at the base and the apex.
*Dorsal edge*.—Narrow ridge from base to apex.

What is claimed:

1. A new and distinct variety of sweet cherry tree as herein illustrated and described.

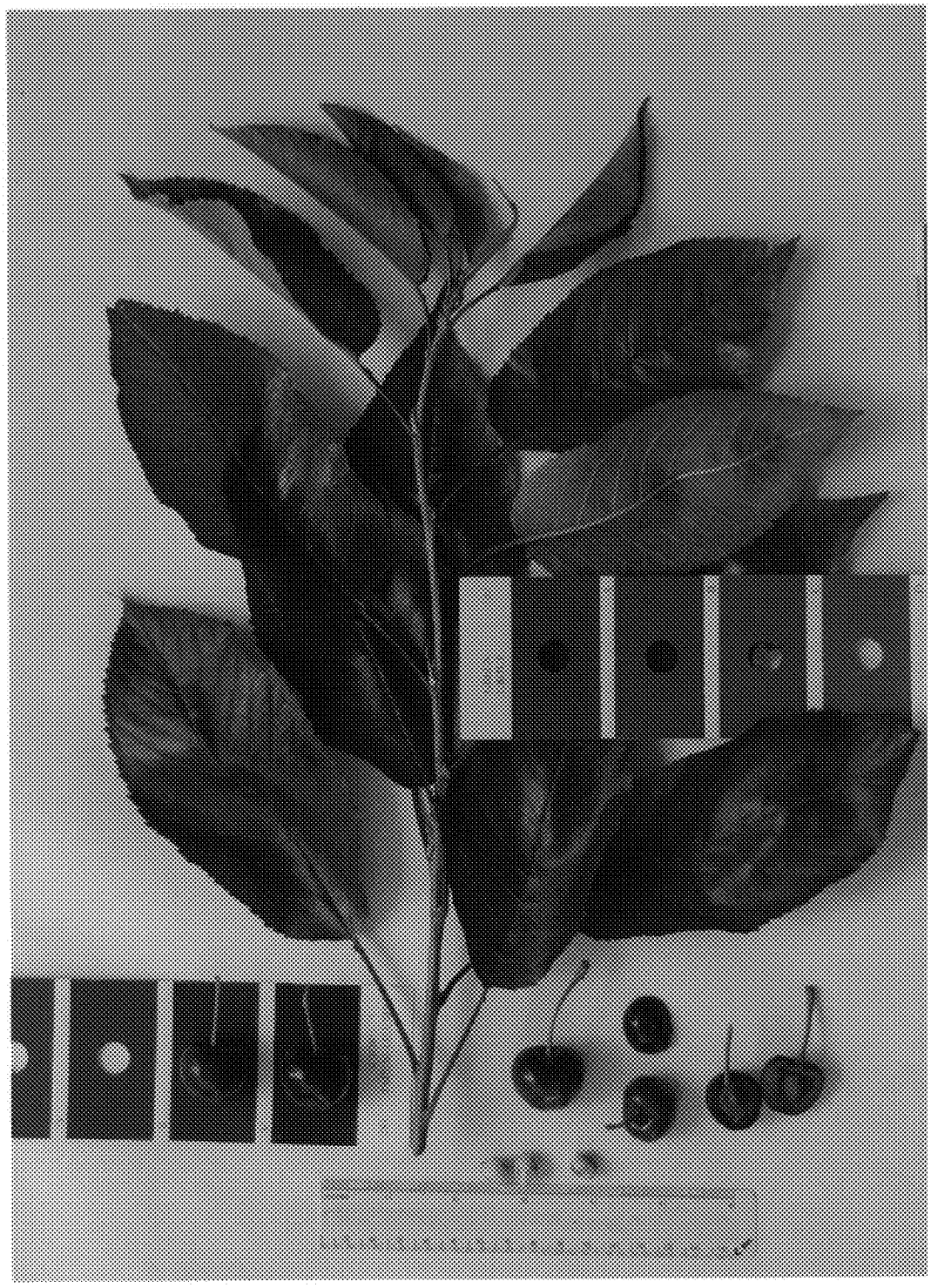

* * * * *